United States Patent [19]
McDow

[11] Patent Number: 5,516,505
[45] Date of Patent: May 14, 1996

[54] METHOD FOR USING CRYOGENIC AGENTS FOR TREATING SKIN LESIONS

[76] Inventor: Ronald A. McDow, 1717 Nottingham Pl., Nashville, Tenn. 37221

[21] Appl. No.: 213,251

[22] Filed: Mar. 14, 1994

Related U.S. Application Data

[63] Continuation-in-part of Ser. No. 4,119, Jan. 13, 1993, Pat. No. 5,330,745, which is a continuation-in-part of Ser. No. 381,296, Jul. 18, 1989, Pat. No. 5,200,170.

[51] Int. Cl.$^6$ .............................. A61L 9/04; A61K 9/08; A61M 35/00; A01N 25/02
[52] U.S. Cl. .............................. 424/45; 424/43; 604/49; 604/289; 604/290; 604/291; 128/DIG. 27
[58] Field of Search ................... 424/43, 45, 47; 128/DIG. 27, 399, 400, 402, 403; 604/49, 219, 289, 290

[56] References Cited

U.S. PATENT DOCUMENTS

| | | | |
|---|---|---|---|
| 4,865,028 | 9/1989 | Swart | 128/303.1 |
| 5,200,170 | 4/1993 | McDow | 424/45 |
| 5,330,745 | 7/1994 | McDow | 424/45 |

*Primary Examiner*—Carlos Azpuru
*Attorney, Agent, or Firm*—Parmelee, Bollinger & Bramblett

[57] ABSTRACT

A method for cryogenically treating skin lesions employing a device for applying cryogenic refrigerant in a liquid pool contacting the area of the skin lesion at a temperature and for a time such that permanent, irreversible rupture of the cellular membrane of the skin cells occurs, wherein the device employs a synthetic plastic foam applicator at the distal end of a tube which may be connected to an aerosol or pressurized container containing the cryogenic refrigerant.

20 Claims, 1 Drawing Sheet

METHOD FOR USING CRYOGENIC AGENTS FOR TREATING SKIN LESIONS

RELATED APPLICATIONS

This application is a Continuation-In-Part of allowed U.S. patent application Ser. No. 08/004,119, filed Jan. 13, 1993, now U.S. Pat. No. 5,330,745, which in turn is a Continuation-In-Part of U.S. patent application Ser. No. 07/381,296, filed Jul. 18, 1989, now U.S. Pat. No. 5,200,170.

FIELD OF THE INVENTION

This invention relates to the field of cryogenic surgery for skin lesions and mucous membranes, including vaginal and cervical lesions and to an improved method for conducting said cryosurgery with various cryogenic agents.

BACKGROUND OF THE INVENTION

Conventional methods of treatment of skin lesions have generally employed conventional surgical methods or a cryogenic method employing liquid nitrogen. Currently, methods used are scalpel (cold steel) surgery, electrodesiccation, and use of liquid nitrogen in cryogenic methods. However, there are a number of significant drawbacks and problems associated with these prior art methods, including, among other things, undue cost, excess time required, complications and the need for expensive storage dewars.

Among the problems associated with the use of liquid nitrogen as a cryogenic agent in heretofore employed cryogenic procedures are (1) a 3–5% evaporation of the liquid nitrogen product while being stored for use, (2) the need for expensive storage dewars for liquid nitrogen generally costing from about $600 to about $2500, (3) expensive delivery systems generally costing from about $700 to about $3000 generally required to spray this cryogen onto the skin and mucous membranes, and (4) occasional permanent hypopigmentation and hypertrophic scarring.

These drawbacks and problems have adversely affected the number of physicians able to perform such operations and the number of patients to receive such treatments for skin lesions.

Among the problems associated with scalpel (cold steel) surgery are (1) bacterial skin infection rates of up to about 18% depending upon, among other things, the sterile technique employed by the operator and heat and humidity of the location of the surgery, (2) hypertrophic scarring which can occur in up to about 25% of patients depending, in general, upon the operator's skill, experience and judgement, and the patient's genetic predisposition to scar, and (3) inefficient use of time. Most scalpel surgery procedures generally require about 25 to 50 minutes to perform. This time is necessitated by the time required for (a) anaesthetizing the treatment area, (b) about 5 minutes waiting period for lidocaine to become optimally effective, (c) time for preparing a sterile operating field, and (d) time for performing the scalpel surgery procedure.

Among the problems associated with electrodesiccation are (1) time consuming need for a local anaesthetic to be applied and become optimally effective and (2) permanent hypertrophic scarring that occurs in a significant percentage of patients undergoing this procedure.

An example of the literature discussing some of these prior art methods and corresponding problems is *Skin Surgery*, Irwin Epstein and Irwin Epstein, Jr., 6th edition, 1987, W. B. Saunders, Philadelphia, Penna., pages 180–182 which includes pictures of facial hypertrophic scarring following curettage and electrodesiccation.

In U.S. Pat. No. 4,865,028 there is taught a method for therapeutic treatment, such as the removal of warts, by local freezing utilizing a cotton wool bud which has been cooled by means of a liquid cryogenic refrigerant present as a liquid in a pressurized container. The cotton wool bud is provided on the end of a hollow rod or capillary tube which is connected to a sealed aerosol container containing the refrigerant, which boils within the temperature range of 0° C. to −50° C., under the pressure of its own gas phase. According to the method of this patent, the cotton wool bud is filled to its saturation drip point. Because cotton is a loose weave and low density swab of irregular shaped fibers having variable interstices, saturation to the drip point thereof results in a waste of cryogenic agent and can produce a dangerous situation, particularly if the refrigerant is flammable to any extent. Moreover, the inconsistent size and shape of the cotton buds as well as the inconsistent weave produce inconsistent treatment results.

It is therefore an object of this invention to provide an improved method for the treatment of skin lesions that substantially eliminates or avoids the aforesaid drawbacks and problems. A further object of this invention is to produce such a method for treating skin lesions which will be less expensive than procedures heretofore used and thus allow more physicians to perform and patients to receive such treatment at much less cost, and which requires less time involved in the procedure and with less side effects or complications, such as infections, hypertrophic scarring and the like. A still further object of this invention is to provide such an improved method for treatment of skin lesions which does not require expensive storage dewars and no need for expensive delivery devices. An even still further object of this invention is to provide such an improved method for treatment of skin lesions requiring up to or about 1/15th of the time required for traditional scalpel surgery or electrodesiccation and curettage which most physicians currently use to treat such skin lesions. A yet still further object is to provide an improved method for treatment of skin lesions in which the potential for human suffering and permanent disfigurement is substantially eliminated or avoided. Additionally, an object of this invention is to provide an improved process for treatment of skin lesions which is more time-efficient and thus saves physician and patient time involved in the procedure. Another additional object of this invention is to provide an improved method for treatment of skin lesions having significant economical and cosmetic benefit to physicians and patients, and which is portable, i.e. is capable of easily being carried from office to office or office to hospital. A still further additional object of this invention is to provide an improved method for treatment of skin lesions which reduces waste of excess cryogenic agent and substantially eliminates dangerous flammable conditions from occurring. Yet another object of this invention is to provide an improved method for treatment of skin lesions wherein the foam applicator can be produced in any desirable shape and thereby provide improved and consistent treatment results. Another object of this invention is for a synthetic foam applicator to provide pressure to the skin lesion being treated in order to effectively decrease the available "heat sink" to rewarm the skin lesion after treatment.

BRIEF DESCRIPTION OF THE DRAWINGS

This invention is to be understood in connection with the drawings which illustrate examples of apparatus and devices suitable for use in carrying out the method of this invention.

BRIEF DESCRIPTION OF THE INVENTION

Figure 1:
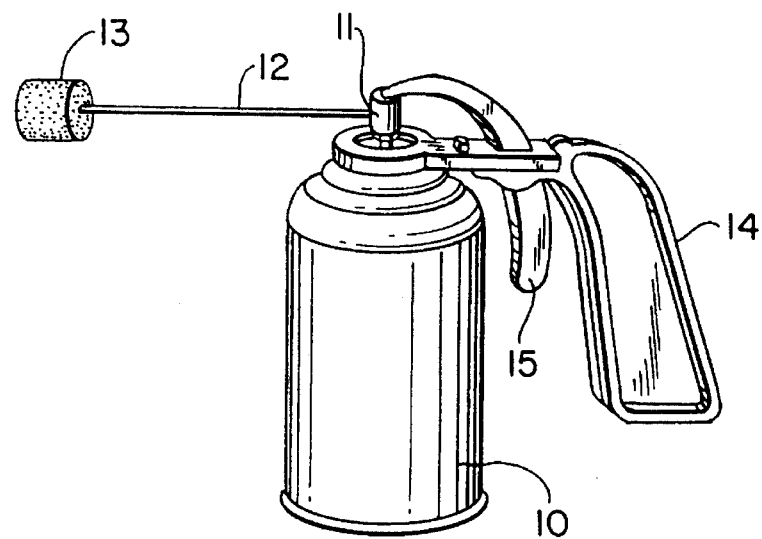
FIG. 1 discloses apparatus for use in the introducing cryogenic agent in the treatment method of this invention.

The method for treatment of skin lesions of this invention comprises a method for cryogenic treatment of skin lesions which permits the use of such method with a wide variety of refrigerants as cryogenic agents. The method of this invention preferably comprises releasing at least an effective amount of the cryogenic agent from an aerosol or pressurized container into a hollow supply tube, such as a capillary tube, so that the cryogenic agent accumulates into a synthetic plastic foam applicator located at the distal end of the tube, contacting the skin surface of a lesion on a human or animal patient with the synthetic plastic foam applicator having the accumulated cryogenic agent for a period of time sufficient to permit cryogenic agent to reduce the temperature of the skin lesion tissue to a temperature to freeze the skin, such that permanent, irreversible rupture of cellular membranes of cells of the skin lesion occurs while the cryogenic agent is evaporating and forming an ice ball, and subsequently removing the synthetic plastic foam applicator from the skin surface after liquid cryogenic agent has evaporated and thereafter permitting the frozen skin tissue of the skin lesion to slowly thaw, preferably over a period of time that is at least about 40 to about 60 seconds.

Although the preferred method of this invention utilizes a synthetic foam applicator located at the distal end of a supply tube connected to a pressurized container, it will be appreciated that, if desired, one could release or spray cryogenic agent from a pressurized container into an open container, such as a styrofoam or metal cup or thermos or like containers, and then dip a synthetic foam applicator, located at one end of any suitable holder, into this open container so that the synthetic foam applicator absorbs the cryogenic agent from the open container into the synthetic foam applicator for direct application to a skin lesion.

This cryogenic method for treatment of skin lesions is believed to be highly effective due to the freeze-thaw cycle that occurs on the skin tissue and the vascular stasis (microcirculatory failure) which develops in the tissue after thawing. The freezing of the skin lesion cells causes intracellular crystal-lization of water, concentration of solute in the cells, and irreversible changes in the cell membranes. The vascular stasis leads to a loss of blood supply and thus essentially deprives the cells of the skin lesion of any possibility of survival.

The method of this invention employs as liquid cryogenic agent any suitable liquid cryogenic agent capable of providing reduced skin temperatures suitable for producing such permanent, irreversible rupture of cellular membranes of cells of the skin lesions when said cryogenic agent is placed on a skin lesion of a patient in accordance with the method of this invention. It is believed that a liquid cryogenic agent reducing the temperature of the skin to a temperature which is no higher than $-20°$ C., preferably no higher than about $-30°$ C., is suitable for use in the method of this invention. As examples of preferred cryogenic agents suitable for use in the method of this invention there can be mentioned such cryogenic agents as chlorodifluoromethane ($CHCLF_2$), dichlorodifluoromethane ($CCl_2F_2$), trifluoromethane ($CHF_3$), 2,2-difluoro-1,1,1-trifluoroethane ($CHCl_2CF_3$), 2-chloro-1,1,1,2-tetrafluoroethane ($CHClFCF_3$), 1,1,1,2,2-pentafluoroethane ($CHF_2CF_3$), 1,1,1,2-tetrafluoroethane ($CH_2FCF_3$), 1,1-dichloro-1-fluoroethane ($CH_3CCl_2F$), 1-chloro-1,1-difluoroethane ($CH_3CClF_2$), and 1,1-difluoroethane ($CH_3CHF_2$), individually or combinations of these cryogenic agents. Since these cryogenic agents evidence essentially no evaporation on storage, no need for expensive storage dewars or expensive delivery devices the method of this invention can be up to $\frac{1}{100}$ of the cost of using liquid nitrogen to treat skin lesions and this is an extremely practical medical advance. Suitable mixtures of the aforementioned suitable cryogenic agents may also be employed.

In general, the suitable cryogenic agents employed in the process of this invention will be non-toxic to both the user and the patient, of either low or non flammability and be considered generally environmentally acceptable to the ozone.

The cryogenic agents or mixtures thereof employed in the method of this invention may have any suitable vapor pressure sufficient to permit packaging thereof in an aerosol or pressurized container, but preferably having a pressure of about 300 psig or less at $130°$ F. ($54.44°$ C.). Mixtures of cryogenic agents may be employed to obtain the preferred vapor pressure. For example, a first cryogenic agent having a vapor pressure of 660 psig at $130°$ F. ($54.44°$ C.) may be mixed with an appropriate amount of a second cryogenic agent having a vapor pressure of only 100 psig at $130°$ F. ($54.44°$ C.). For example, a 50% mixture of 1,1,2,2-tetrafluoroethane (134a) having a vapor pressure of 199.8 psig with 50% of pentafluoroethane (125) having a vapor pressure of 380.3 psig provides a composition having a vapor pressure of 290.05 psig at $130°$ F. ($54.44°$ C.). Similarly, a mixture of 15% 1,1-difluoroethane (152a) having a vapor pressure of 177.0 psig, 45% 1,1,1,2-tetrafluoroethane (134a) having a vapor pressure of 199.8 psig and 40% pentafluoroethane (125) having a vapor pressure of 380.3 psig provides a composition having a vapor pressure of 268.58 at $130°$ F. ($54.44°$ C.). The mixtures of cryogenic agents should be sufficiently stable not only to provide an acceptable skin lesion removal procedure but also to remain chemically stable when stored in an aerosol or pressurized container for several years. If necessary, commonly known non-toxic chemical stabilizers which do not adversely affect the skin lesion removal procedure may be added to the cryogenic agents to obtain the desired stability.

DETAILED DESCRIPTION OF THE INVENTION

The use of the cryogenic agents in accordance with the method of this invention will generally reduce the skin temperature of the cells of the skin lesion to a temperature which is no higher than about $-20°$ C., preferably no higher than about $-30°$ C., and even more preferably no higher than about $-50°$ C. In general the method of treatment in accordance with this invention will generally produce a 2 mm to 15 mm pool of liquid cryogenic agent on the skin lesion and thereby reduce the temperature to a skin temperature within the range of from about $-30°$ C. to about $-120°$ C. in order to cause suitable destruction (necrosis) of the cells of the of the skin lesion.

Rapid freezing of the cells promotes increased cellular destruction. Also, slow, unassisted thawing which lasts at least about 40 to about 60 seconds increases cellular destruction. Thus, suitable cryogenic agents with longer thaw times, generally from about 40 to about 60 seconds or longer, are generally preferred. The ability of suitable cryogenic agents to be effectively employed in the method of this invention thus, in part, resides in their ability to freeze rapidly the cells of the skin lesions and then thaw slowly which is believed to be a function, at least in part, of both the boiling point of the cryogenic agent and its latent heat of vaporization. For example, although the boiling point of dichlorodifluoromethane is −29.8° C. actual freezing temperatures as low as −60° C. using cryoprobes have been recorded.

Although many skin lesions may be suitably treated and removed by the steps of the method set forth in the hereinbefore Brief Description of the Invention section of this application, it is often desirable and highly beneficial that after permitting the skin lesion to thaw completely after removing the synthetic plastic foam applicator, to sequentially repeat the method. Such repetition of freeze-thaw cycles promotes increased cellular destruction and thus improved removal of skin lesions.

Although the suitable length of time employed for introducing the cryogenic agent from the synthetic plastic foam applicator onto the skin lesion surface can vary widely depending, at least in part, upon the type of skin lesion, its size and thickness, it has been found that a period of from about 20 to about 35 seconds is generally suitable for epithelial skin lesions that are benign. Cryogenic agent is pooled on the skin lesion in the synthetic plastic foam applicator and freezes skin cells.

After evaporation of the cryogenic agent the freezing is completed and the synthetic plastic foam applicator is removed from the skin surface, the skin lesions are frozen and appear white. This signals the beginning of the thaw stage which generally amounts to a period of about 40 to about 60, preferably about 45 to 55 seconds.

The synthetic plastic foam applicators suitable for use in this invention are any synthetic foam applicators able to accumulate or absorb liquid cryogenic agents. As examples of such suitable synthetic foam that may be formed into applicators for use in this invention there may be mentioned polyurethanes, polyolefin foams such as polyethylene and polypropylene, phenolic polymer foam, polyvinyl chloride foams and polystyrene foams. Synthetic plastic foams of both high and low density may be employed. Especially preferred for use in this invention is a flexible high density polyurethane foam. A more rigid synthetic foam applicator should be used if significant pressure on the skin lesion is desired.

The synthetic foam applicators may be synthesized in the desired shape or can be produced into the desired shape after synthesis. The foam applicator can be in any suitable shape for use in the method of this invention, such as a spherical, oval or cubical shaped applicator or any other suitable shape for application to the area of the skin lesion.

The synthetic plastic foam applicators are highly absorbent and predictable as to the amount of cryogenic agent needed for saturation. In addition, the synthetic foam applicator is able to hold liquid cryogenic agent for a longer period of time. As a result, the evaporation rate of liquid cryogenic agent is slower and thereby allows a more efficient skin lesion removal procedure.

The method of this invention is suitable for use in treating a wide variety of skin lesions and mucous membranes, including vaginal and cervical lesions, particularly verruca and seborrheic keratoses. Among the many skin lesions that may be treated according to the method of this invention there may be mentioned, for example, melanocytes, osteocytes, lentigo (age spots), seborrheic keratoses, actinic keratoses, achrochordon, molluscum contagiosum, verruca digitata lesions, verruca periungual lesions, verruca filiformis lesions, verruca glabra lesions, verruca plana lesions, verruca plantaris lesions, verruca vulgaris lesions, and venereal warts.

Other treatable lesions by this process include mucocele, porokeratosis plantaris discreta, sebaceous hyperplasia, condylomata acuminatum (venereal warts), generalized acne, acne keloidalis, acne rosacea, angioma, venous lakes, chondrodermatitis, granuloma pyogenicum, hidradenitis suppurativa, keloids keratoacanthoma, leukoplakia, steatocystoma multiplex, trichiasis, superficial epithelial nevus, junctional nevus, pyogenic granuloma, carbuncle, prurigo nodularis, lentigo maligna, dermatofibroma, adenoma sebaceum.

If the effective temperature produced by the agents or combination of agents is −50° C. or lower and verifiable, then basal cell carcinomas and squamous cell carcinomas may also be treated by this process.

The method of this invention is illustrated but not limited by reference to the figures in the drawings. As an example of the best ways of carrying out the operation of the method of this invention, FIG. 1 discloses a cryogenic agent packaged in a container 10, preferably a 12 or 16 ounce aerosol or pressurized container, and dispensed through an aerosol nozzle 11. A hollow supply tube 12, preferably a 1 mm capillary tube, is attached to the aerosol nozzle 11 to direct spray accurately into a synthetic plastic foam applicator 13 located at the distal end of tube 12. The container may also be provided with a snap-on handle 14 and trigger device 15 as illustrated in FIG. 1 for ease of operation in dispensing cryogenic agent from the container into the synthetic plastic foam applicator in a manner that permits an appropriate or metered amount of cryogenic agent to be dispensed while protecting the user's hands and fingers from freezing.

Figure 2:
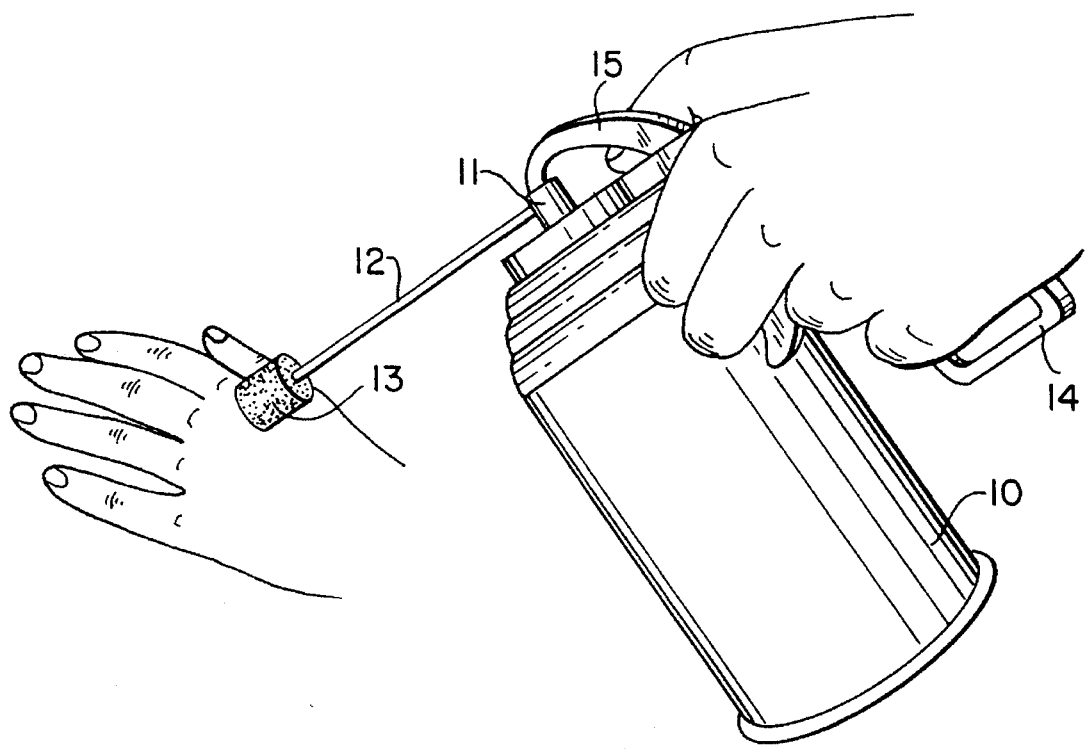
FIG. 2 demonstrates the treatment method of this invention.

FIG. 2 demonstrates the use of the apparatus to perform the method of this invention. The cryogenic agent is sprayed from the container 10 through the capillary tube 12 into the synthetic plastic foam applicator 13 and the applicator is then held in position on a patient's skin in a manner to seal against the patient's skin in the area of the skin lesion.

Although the synthetic plastic foam applicator in FIGS. 1 and 2 is shown to be a cylindrical foam applicator having a circular end for contacting the skin in the area of the skin lesion, it will be appreciated that the foam applicator may be of any suitable or desirable shape or size, such as for example, a cubical applicator, a rectangular applicator, a spherical applicator or an oval applicator, and the like.

A specifically designed oval, cylindrical, rectangular, or other unique synthetic foam applicator can be used to provide a pressure application to the lesion being treated in addition to containing the actual cryogenic agent(s). By applying consistent pressure to the lesion being treated, superficial capillaries, veins and arteries that are immediately surrounding, underneath and within the lesion are compressed reducing the total "heat sink" available to thaw and rewarm the lesion. The synthetic foam applicator filled with cryogenic agent is applied directly to the lesion for a previously prescribed period of time. The benefits provided by this simultaneous pressure and cryogen contact are: (1) deeper cryogenic destruction of tissue will be achieved without increasing the total freeze time; (2) a shorter freeze time will be necessary for ice ball formation to occur (this increases the time efficiency of the procedure and decreases total pain experienced by the patient) and, (3) cryogenic agent(s) with somewhat higher boiling points can now be used more effectively. This improved process will significantly improve treatment effectiveness for all lesions by this method. It now becomes especially feasible to treat vascular lesions, such as for example, hemangiomas and lymphangiomas, by this method since because of their very vascular nature they have very large "heat sinks" which tend to thaw very rapidly or prevent actual ice ball formation.

The method of this invention is further illustrated by the following example.

EXAMPLE

Dichlorodifluoromethane ($CCl_2F_2$) is sprayed from 12 to 16 ounce aerosol containers through a one millimeter capillary applicator tube measuring 13 cm in length, to a high density cylindrical, polyurethane foam applicator at the distal end of the tube until a metered or saturation effective amount of the cryogenic agent is absorbed or occluded in the synthetic plastic foam applicator. The circular end of the polyurethane foam applicator containing the absorbed cryogenic agent is then placed in contact with the area of skin lesion to be treated and held in contact with the skin surface for a period of about 30 seconds until the dichlorodifluoromethane evaporates and the lesion being treated turns white, after which the polyurethane foam applicator is removed. This represents the beginning of the thaw stage which averages about 40 to 60 seconds. Extreme care must be taken not to touch the lesions during this thaw stage. The heat from a finger or other body part would decrease the thaw time and diminish the cellular destructive potential of the cryogen. A second and third freeze-thaw cycle may be performed depending upon the thickness and width of the lesion being treated. Lidocaine may be used as a local anaesthetic prior to freezing in extremely sensitive patients but it is usually not necessary. Post-operative care includes leaving the lesion exposed to air unless a drainage develops, cleaning the lesion with peroxide daily, and allowing the ensuing crust formation to spontaneously detach.

Similar treatment methods can be performed using chlorodifluoromethane, trifluoromethane, 2,2-difluoro-1,1,1-trifluoroethane, 2-chloro-1,1,1,2-tetrafluoroethane, 1,1,1,2,2-penta-fluoroethane, 1,1,1,2-tetrafluoroethane, 1,1-dichloro-1-fluoroethane, 1-chloro-1,1-difluoroethane, 1,1-difluoroethane, and suitable mixtures of such cryogenic agents or using polyethylene, polypropylene, phenolic, polyvinyl chloride or polystyrene foam applicators of any suitable shape.

With the foregoing description of the invention, those skilled in the art will appreciate that modifications may be made to the invention without departing from the spirit thereof. Therefore, it is not intended that the scope of the invention be limited to the specific embodiments illustrated and described.

I claim:

1. A method of cryogenically treating a lesion on the surface of skin comprising the steps of:
  (a) releasing at least an effective amount of a cryogenic agent from an aerosol or pressurized container in a manner such that the cryogenic agent accumulates into a synthetic plastic foam applicator,
  (b) contacting the skin surface of a lesion with the synthetic plastic foam applicator having the accumulated cryogenic agent for a period of time sufficient to permit the cryogenic agent to reduce the temperature of the skin lesion tissue to a temperature to freeze the skin tissue such that permanent, irreversible rupture of cellular membranes of cells of the skin lesion occurs while the cryogenic agent is evaporating,
  (c) subsequently removing the synthetic plastic foam applicator from the skin surface after liquid cryogenic agent has evaporated, and
  (d) thereafter permitting the frozen skin tissue of the skin lesion to slowly thaw.

2. The method of claim 1 wherein the cryogenic agent is released from an aerosol or pressurized container into an open container and the synthetic foam applicator is placed into the open container to absorb cryogenic agent from the open container for application of the cryogenic agent to the skin lesion.

3. The method of claim 2 comprising sequentially repeating steps b), c) and d) of said method.

4. A method of cryogenically treating a lesion on the surface of skin comprising the steps of:
  (a) releasing at least an effective amount of a cryogenic agent from an aerosol or pressurized container into a hollow supply tube attached at one end to said container so that said cryogenic agent accumulates into a synthetic plastic foam applicator located at a distal end of said supply tube,
  (b) contacting the skin surface of a lesion with the synthetic plastic foam applicator having the accumulated cryogenic agent for a period of time sufficient to permit the cryogenic agent to reduce the temperature of the skin lesion tissue to a temperature to freeze the skin tissue such that permanent, irreversible rupture of cellular membranes of cells of the skin lesion occurs while the cryogenic agent is evaporating,
  (c) subsequently removing the synthetic plastic foam applicator from the skin surface after liquid cryogenic agent has evaporated, and
  (d) thereafter permitting the frozen skin tissue of the skin lesion to slowly thaw.

5. The method of claim 4 further comprising sequentially repeating the steps a), b), c) and d) of said method.

6. The method according to claim 4 in which said step of contacting the skin surface of a skin lesion with the synthetic plastic foam applicator continues for a time period of about 20 to about 35 seconds.

7. The method according to claim 6 in which the step of permitting the skin lesion to thaw occurs over a period of time of at least about 40 seconds.

8. The method of claim 1 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

9. The method of claim 4 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

10. The method of claim 7 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane, 1,1-difluoroethane, methane, propane, isobutane, n-butane, dimethyl ether and mixtures of such cryogenic agents.

11. The method of claim 1 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

12. The method of claim 4 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

13. The method of claim 7 wherein the cryogenic agent is selected from the group consisting of chlorodifluoromethane, dichlorodifluoromethane, trifluoromethane, 2,2-difluoro-1,1,1-trifluoroethane, 2-chloro-1,1,1,2-tetrafluoroethane, 1,1,1,2,2-pentafluoroethane, 1,1,1,2-tetrafluoroethane, 1,1-dichloro-1-fluoroethane, 1-chloro-1,1-difluoroethane and 1,1-difluoroethane.

14. The method of claim 10 wherein the skin lesion being treated is a lesion selected from the group consisting of lentigo, seborrheic keratoses, actinic keratoses, achrochordon, molluscum contagiosum, verruca digitata lesions, verruca periungual lesions, verruca filiformis lesions, verruca glabra lesions, verruca plana lesions, verruca plantaris lesions, verruca vulgaris lesions, venereal warts, mucocele, porokeratosis plantaris discreta, sebaceous hyperplasia, condylomata acuminatum, generalized acne, acne keloidalis, acne rosacea, angioma, venous lakes, chondrodermatitis, granuloma pyogenicum, hidradenitis suppurativa, keloids, keratoacanthoma, leukoplakia, steatocystoma multiplex, trichiasis, superficial epithelial nevus, junctional nevus, pyogenic granuloma, carbuncle, prurigo nodularis, lentigo malign, dermatofibroma, adenoma sebaceum, basal cell carcinomas and squamous cell carcinomas.

15. The method of claim 1 wherein the synthetic plastic foam applicator is selected from the group consisting of: polyurethane, polyethylene, polypropylene, phenolic, polystyrene and polyvinyl chloride foam applicators.

16. The method of claim 4 wherein the synthetic plastic foam applicator is selected from the group consisting of: polyurethane, polyethylene, polypropylene, phenolic, polystyrene and polyvinyl chloride foam applicators.

17. The method of claim 7 wherein the synthetic plastic foam applicator is selected from the group consisting of: polyurethane, polyethylene, polypropylene, phenolic, polystyrene and polyvinyl chloride foam applicators.

18. The method of claim 8 wherein the synthetic plastic foam applicator is selected from the group consisting of: polyurethane, polyethylene, polypropylene, phenolic, polystyrene and polyvinyl chloride foam applicators.

19. The method of claim 14 wherein the synthetic plastic foam applicator is selected from the group consisting of: polyurethane, polyethylene, polypropylene, phenolic, polystyrene and polyvinyl chloride foam applicators.

20. The method of claim 16 wherein the synthetic plastic foam applicator is a high density polyurethane foam applicator.

* * * * *